(12) United States Patent
Liu

(10) Patent No.: US 11,779,314 B2
(45) Date of Patent: Oct. 10, 2023

(54) MOBILE INFORMATION AND CONTROL TERMINAL FOR ULTRASONIC DIAGNOSTIC SYSTEMS AND METHODS OF USING THE SAME

(71) Applicant: Shijian Liu, Shanghai (CN)

(72) Inventor: Shijian Liu, Shanghai (CN)

(73) Assignee: SHANGHAI WEILING ELECTRONICS CO., LTD, Shanghai (CN)

( * ) Notice: Subject to any disclaimer, the term of this patent is extended or adjusted under 35 U.S.C. 154(b) by 188 days.

(21) Appl. No.: 17/557,493

(22) Filed: Dec. 21, 2021

(65) Prior Publication Data

US 2022/0110610 A1 Apr. 14, 2022

Related U.S. Application Data

(62) Division of application No. 16/218,171, filed on Dec. 12, 2018, now Pat. No. 11,364,016.

(51) Int. Cl.
*A61B 8/14* (2006.01)
*A61B 8/00* (2006.01)
*G16H 15/00* (2018.01)
*G16H 40/67* (2018.01)

(52) U.S. Cl.
CPC ............... *A61B 8/54* (2013.01); *A61B 8/565* (2013.01); *G16H 15/00* (2018.01); *G16H 40/67* (2018.01)

(58) Field of Classification Search
CPC .......... A61B 8/54; A61B 8/565; G16H 10/60; G16H 15/00; G16H 30/20; G16H 40/67; G16H 50/20; G16H 80/00
See application file for complete search history.

(56) References Cited

U.S. PATENT DOCUMENTS

2015/0035959 A1* 2/2015 Amble ................ A61B 5/0077
348/74

* cited by examiner

*Primary Examiner* — Mark D Remaly
(74) *Attorney, Agent, or Firm* — Ming Jiang; MM IP SERVICES LLC

(57) ABSTRACT

Aspects of present disclosure relates to mobile information and control terminals for ultrasonic diagnostic systems and the ultrasonic diagnostic systems. In certain embodiments, ultrasonic diagnostic system includes: a mobile information and control terminal, a local host in a first location, a remote host connected to an ultrasonic diagnostic imaging system in a second location, and a communication network. Mobile information and control terminal is operated by an ultrasonic diagnostic expert in the first location. Mobile information and control terminal retrieves patient information of a patient from patient database, provides ultrasonic diagnostic control instructions from ultrasonic diagnostic expert to ultrasonic diagnostic technicians in second location. An ultrasonic diagnostic technician performs ultrasonic diagnostic examination on patient according to ultrasonic diagnostic control instructions and transmits patient ultrasonic diagnosis information back to local host and ultrasonic diagnostic expert in real time. The ultrasonic diagnostic expert then generates and displays ultrasonic diagnosis reports of patient.

8 Claims, 7 Drawing Sheets

MOBILE INFORMATION AND CONTROL TERMINAL FOR ULTRASONIC DIAGNOSTIC SYSTEMS AND METHODS OF USING THE SAME

FIELD

The present disclosure generally relates to ultrasonic diagnostic technology, and more particularly to a mobile information and control terminal for an ultrasonic diagnostic system, an ultrasonic diagnostic system and methods of using the ultrasonic diagnostic system.

BACKGROUND

Ultrasonic diagnostic system is a diagnostic imaging technique based on the application of ultrasound. It is used to see internal body structures such as tendons, muscles, joints, blood vessels, and internal organs. Its aim is often to find a source of a disease or to exclude any pathology. The practice of examining pregnant women using ultrasound is called obstetric ultrasound, and is widely used.

Ultrasound is sound waves with frequencies which are higher than those audible to humans (>20,000 Hz). As illustrated in FIG. 6, ultrasonic images, also known as sonograms, are made by sending pulses of ultrasound into tissue of a patient 602 using a probe 612 by an ultrasonic diagnostic technician 601 or an ultrasonic diagnostic expert. The sound echoes off the tissue; with different tissues reflecting varying degrees of sound. These echoes are recorded and displayed as an image on a display device 611 of an ultrasonic diagnostic imaging system 610 to the ultrasonic diagnostic expert. The ultrasonic diagnostic expert is usually a skilled and experienced radiologist who maneuvers the probe 612 in various angles and positions in real time to get a clear understanding of the patient's disease and to obtain conclusive diagnosis. Such an expert is scarce resource, and may not be available in many areas such as rural areas and many remote countryside locations. Currently, many ultrasonic diagnostic experts have to travel to these areas to perform ultrasonic diagnosis, which makes ultrasonic diagnostic technology very expensive for the patients in these areas. Sometimes its costs make it impossible to perform ultrasonic diagnosis in these areas, and sometimes the patients from these areas may have to travel to major cities to access such ultrasonic diagnostic systems. It is desirable to have an ultrasonic diagnostic system that allows an ultrasonic diagnostic expert in anywhere to perform ultrasonic diagnosis on a patient in a different location with helps from an ultrasonic diagnostic technician 601 and without forcing either the ultrasonic diagnostic expert or the patient to travel to the same location.

Therefore, heretofore unaddressed needs still exist in the art to address the aforementioned deficiencies and inadequacies.

SUMMARY

In one aspect, the present disclosure relates to a mobile information and control terminal for an ultrasonic diagnostic system. In certain embodiments, the mobile information and control terminal includes: an information interface, a control interface, an information multiplexer, and a network interface, a processor, and a memory. The information interface receives and transmits ultrasonic diagnosis information between the mobile information and control terminal, a local host in a first location, and a remote host in a second location through one or more information channels. The control interface receives ultrasonic diagnostic control instructions from an ultrasonic diagnostic expert and transmits the ultrasonic diagnostic control instructions to the local host, and the remote host through one or more control channels. The information multiplexer receives, exchanges and transmits the ultrasonic diagnosis information through the one or more information channels in the ultrasonic diagnostic system. The network interface connects the mobile information and control terminal to a communication network.

In certain embodiments, the memory includes comprises random access memory (RAM) for supporting the operation of the processor, and a non-volatile storage device (NVSD). The non-volatile storage device stores an operating system, and computer executable instructions. When executed on the processor, the computer executable instructions cause the processor to perform: establishing network connection between the mobile information and control terminal, the local host in the first location, a patient database and the remote host in the second location through the network interface over the communication network, and retrieving, by the mobile information and control terminal, the patient information of a patient from the patient database. The computer executable instructions cause the processor to perform: instructing, by an ultrasonic diagnostic expert in the first location, an ultrasonic diagnostic technician in the second location using the ultrasonic diagnostic control instructions through the one or more control channels, performing, by the ultrasonic diagnostic technician, ultrasonic diagnostic examination on the patient interactively according to the ultrasonic diagnostic control instructions, receiving, by the mobile information and control terminal, ultrasonic diagnosis information from the ultrasonic diagnostic technician in real time, and generating, via the mobile information and control terminal by the ultrasonic diagnostic expert, an ultrasonic diagnosis report and transmitting the ultrasonic diagnosis report to a doctor of the patient and the patient database.

In certain embodiments, the one or more information channels include: a first information channel $I_1$, a second information channel $I_2$, . . . , and an M-th information channel $I_M$, where M is a positive integer. The one or more information channels include: one or more patient information channel for transmission of the patient information, one or more information channels from the local host to the remote host for demonstrations by the ultrasonic diagnostic expert, one or more information channels from the remote host to the local host for real time ultrasonic diagnosis by the ultrasonic diagnostic technician, and one or more ultrasonic diagnosis report transmission channels.

In certain embodiments, the one or more control channels include: a first control channel $C_1$, a second control channel $C_2$, . . . , and an N-th control channel $C_N$, wherein N is a positive integer. The one or more control channels include: one or more audio signal transmission channels, one or more image signal transmission channels, one or more video signal transmission channels, and one or more robotic control signal transmission channels.

In another aspect, the present disclosure relates to an ultrasonic diagnostic system. In certain embodiments, the ultrasonic diagnostic system includes: a mobile information and control terminal, a local host in a first location, a remote host connected to an ultrasonic diagnostic imaging system in a second location, and a communication network. The mobile information and control terminal is connected to the communication network and operated by an ultrasonic diagnostic expert located in the first location. The mobile information and control terminal retrieves patient information of a patient from a patient database, provides ultrasonic diagnostic control instructions from the ultrasonic diagnostic expert, receives patient ultrasonic diagnosis information, and generates and displays ultrasonic diagnosis reports of the patient.

In certain embodiments, the local host is connected to the communication network and retrieves the patient information of the patient from the patient database, providing ultrasonic diagnostic control instructions from the ultrasonic diagnostic expert, and receiving ultrasonic diagnosis information, generating and displaying ultrasonic diagnosis reports of the patient. The remote host is connected to the ultrasonic diagnostic imaging system in the second location. An ultrasonic diagnostic technician performs ultrasonic diagnostic examination on the patient with the ultrasonic diagnostic imaging system according to the ultrasonic diagnostic control instructions received from the ultrasonic diagnostic expert and generates and transmits ultrasonic diagnosis information to the ultrasonic diagnostic expert. The communication network connects the mobile information and control terminal, the local host, the remote host, and the patient database through one or more information channels and one or more control channels.

In certain embodiments, the ultrasonic diagnostic system retrieves the patient information of the patient from the patient database, receives the ultrasonic diagnostic control instructions from the ultrasonic diagnostic expert through the mobile information and control terminal, instructs the ultrasonic diagnostic technician to perform ultrasonic diagnostic examination on the patient in the second location, receives real time ultrasonic diagnosis information interactively from the remote host, generates and displays the ultrasonic diagnosis information of the patient, and transmits the ultrasonic diagnosis information of the patient to the remote host and the patient database.

In certain embodiments, the communication network includes: a wireless personal area network (WPAN), a wireless local area network (WLAN), a wireless metropolitan area network (WMAN), a wireless wide area network (WWAN), a cellular network, a mobile communication network, and any combinations of these networks. The wireless personal area network (WPAN) may include a Wi-Fi network; a Bluetooth network, an infrared network, and a Zigbee network.

In certain embodiments, the one or more information channels include: a first information channel $I_1$, a second information channel $I_2$, . . . , and an M-th information channel $I_M$, where M is a positive integer. The one or more information channels include: one or more patient information channel for transmission of the patient information, one or more information channels from the local host to the remote host for demonstrations by the ultrasonic diagnostic expert, one or more information channels from the remote host to the local host for real time ultrasonic diagnosis by the ultrasonic diagnostic technician, and one or more ultrasonic diagnosis report transmission channels.

In certain embodiments, the one or more control channels include: a first control channel $C_1$, a second control channel $C_2$, . . . , and an N-th control channel $C_N$, wherein N is a positive integer. The one or more control channels include: one or more audio signal transmission channels, one or more image signal transmission channels, one or more video signal transmission channels, and one or more robotic control signal transmission channels.

In certain embodiments, the mobile information and control terminal is connected to one or more information display devices. The one or more information display devices include: one or more flat panel televisions (TVs), high definition televisions (HDTVs), and ultra-high-definition televisions (UHDTVs), one or more TVs, HDTVs, and UHDTVs having touch control panels, one or more computer monitors, one or more computer monitors having touch control panels, one or more smart phones, one or more tablet computers, one or more personal digital assistant (PDA) devices, one or more optical projectors, one or more laser projectors, and any combinations of these display devices.

In certain embodiments, each of the one or more information display devices is partitioned to display one or more ultrasonic diagnosis information and results from the one or more information channels.

In certain embodiments, the local host includes: a local information interface, a local control interface, a local network interface, a local information multiplexer, a local processor and a local memory. The local information interface receives and transmits ultrasonic diagnosis information between the local host and the remote host through the one or more information channels. The local control interface receives the ultrasonic diagnostic control instructions from the ultrasonic diagnostic expert through the mobile information and control terminal and transmits the ultrasonic diagnostic control instructions to the remote host through the one or more control channels. The local network interface connects the local host to the communication network. The local information multiplexer receives, exchanges and transmits the ultrasonic diagnosis information through the one or more information channels in the ultrasonic diagnostic system.

In certain embodiments, the local memory includes random access memory (RAM) for supporting the operation of the local processor, and a non-volatile storage device (NVSD). The non-volatile storage device (NVSD) stores an operating system, and computer executable instructions. When executed on the local processor, the computer executable instructions cause the local processor to perform: establishing network connection between the mobile information and control terminal, the local host in the first location through the local network interface, the patient database and the remote host in the second location through a remote network interface over the communication network, and retrieving, by the local host, the patient information of the patient from the patient database. The computer executable instructions further cause the local processor to perform: instructing, by sending the ultrasonic diagnostic control instructions to the ultrasonic diagnostic technician in the second location to perform ultrasonic diagnostic examination on the patient interactively according to the ultrasonic diagnostic control instructions, receiving, from the remote host, ultrasonic diagnosis information interactively in real time, and generating, by the ultrasonic diagnostic expert, an ultrasonic diagnosis report and transmitting the ultrasonic diagnosis report to a doctor of the patient and the patient database.

In certain embodiments, the remote host includes: a remote information interface, a remote control interface, the remote network interface, a remote information multiplexer, a remote processor and a remote memory. The remote information interface receives and transmits ultrasonic diagnosis information between the local host and the remote host through the one or more information channels. The remote control interface receives the ultrasonic diagnostic control instructions from the ultrasonic diagnostic expert through the mobile information and control terminal over the one or more control channels. The remote network interface connects the remote host to the communication network. The remote information multiplexer receives, exchanges and transmits the ultrasonic diagnosis information through the one or more information channels in the ultrasonic diagnostic system.

In certain embodiments, the remote memory includes random access memory (RAM) for supporting the operation of the remote processor, and a non-volatile storage device (NVSD). The non-volatile storage device (NVSD) stores an operating system and computer executable instructions. When executed on the remote processor, the computer executable instructions cause the remote processor to perform: establishing network connection to the patient database and the remote host in the second location through the remote network interface over the communication network, and receiving, by the ultrasonic diagnostic technician in the second location, the ultrasonic diagnostic control instructions. The computer executable instructions further cause the remote processor to perform: instructing the ultrasonic diagnostic technician to perform ultrasonic diagnostic examination on the patient interactively according to the ultrasonic diagnostic control instructions, transmitting ultrasonic diagnosis information to the ultrasonic diagnostic expert interactively in real time through the one or more information channels, and receiving, by the ultrasonic diagnostic technician, an ultrasonic diagnosis report of the patient from the ultrasonic diagnostic expert.

In yet another aspect, the present disclosure relates to a method of using an ultrasonic diagnostic system. In certain embodiments, the method includes: installing a local host in a first location where an ultrasonic diagnostic expert is performing ultrasonic diagnosis using ultrasonic diagnostic control instructions via a mobile information and control terminal, installing a remote host in a second location where an ultrasonic diagnostic technician is performing ultrasonic diagnostic examination on a patient using an ultrasonic diagnostic imaging system according to the ultrasonic diagnostic control instructions from the ultrasonic diagnostic expert, connecting the mobile information and control terminal, the local host, the remote host, a patient database to a communication network through one or more information channels and one or more control channels, and retrieving, by the mobile information and control terminal, patient information of the patient from the patient database and displaying the retrieved patient information to the ultrasonic diagnostic expert.

In certain embodiments, the method also includes: providing, by the ultrasonic diagnostic expert in the first location, ultrasonic diagnostic control instructions to the ultrasonic diagnostic technician through the one or more control channels, receiving, by the ultrasonic diagnostic technician in the second location, the ultrasonic diagnostic control instructions and performing ultrasonic diagnostic examination on the patient interactively according to the ultrasonic diagnostic control instructions, transmitting, by the ultrasonic diagnostic technician, ultrasonic diagnosis information to the ultrasonic diagnostic expert interactively in real time through the one or more information channels, and generating, by the ultrasonic diagnostic expert, an ultrasonic diagnosis report, and transmitting the ultrasonic diagnosis report to a doctor of the patient and the patient database.

In certain embodiments, the communication network includes: a wireless personal area network (WPAN), a wireless local area network (WLAN), a wireless metropolitan area network (WMAN), a wireless wide area network (WWAN), a cellular network, a mobile communication network, and any combinations of these networks. The wireless personal area network (WPAN) may include a Wi-Fi network; a Bluetooth network, an infrared network, and a Zigbee network.

In certain embodiments, the one or more information channels include: a first information channel $I_1$, a second information channel $I_2$, . . . , and an M-th information channel $I_M$, where M is a positive integer. The one or more information channels include: one or more patient information channel for transmission of the patient information, one or more information channels from the local host to the remote host for demonstrations by the ultrasonic diagnostic expert, one or more information channels from the remote host to the local host for real time ultrasonic diagnosis by the ultrasonic diagnostic technician, and one or more ultrasonic diagnosis report transmission channels.

In certain embodiments, the one or more control channels include: a first control channel $C_1$, a second control channel $C_2$, . . . , and an N-th control channel $C_N$, wherein N is a positive integer. The one or more control channels include: one or more audio signal transmission channels, one or more image signal transmission channels, one or more video signal transmission channels, and one or more robotic control signal transmission channels.

In certain embodiments, the mobile information and control terminal is connected to one or more information display devices. The one or more information display devices include: one or more flat panel televisions (TVs), high definition televisions (HDTVs), and ultra-high-definition televisions (UHDTVs), one or more TVs, HDTVs, and UHDTVs having touch control panels, one or more computer monitors, one or more computer monitors having touch control panels, one or more smart phones, one or more tablet computers, one or more personal digital assistant (PDA) devices, one or more optical projectors, one or more laser projectors, and any combinations of these display devices.

In certain embodiments, each of the one or more information display devices is partitioned to display one or more ultrasonic diagnosis information and results from the one or more information channels.

In certain embodiments, the local host includes: a local information interface, a local control interface, a local network interface, a local information multiplexer, a local processor and a local memory. The local information interface receives and transmits ultrasonic diagnosis information between the local host and the remote host through the one or more information channels. The local control interface receives the ultrasonic diagnostic control instructions from the ultrasonic diagnostic expert through the mobile information and control terminal and transmits the ultrasonic diagnostic control instructions to the remote host through the one or more control channels. The local network interface connects the local host to the communication network. The local information multiplexer receives, exchanges and transmits the ultrasonic diagnosis information through the one or more information channels in the ultrasonic diagnostic system.

In certain embodiments, the local memory includes random access memory (RAM) for supporting the operation of the local processor, and a non-volatile storage device (NVSD). The non-volatile storage device (NVSD) stores an operating system, and computer executable instructions. When executed on the local processor, the computer executable instructions cause the local processor to perform: establishing network connection between the mobile information and control terminal, the local host in the first location through the local network interface, the patient database and the remote host in the second location through a remote network interface over the communication network, and retrieving, by the local host, the patient information of the patient from the patient database. The computer executable instructions further cause the local processor to perform: instructing, by sending the ultrasonic diagnostic control instructions to the ultrasonic diagnostic technician in the second location to perform ultrasonic diagnostic examination on the patient interactively according to the ultrasonic diagnostic control instructions, receiving, from the remote host, ultrasonic diagnosis information interactively in real time, and generating, by the ultrasonic diagnostic expert, an ultrasonic diagnosis report and transmitting the ultrasonic diagnosis report to a doctor of the patient and the patient database.

In certain embodiments, the remote host includes: a remote information interface, a remote control interface, the remote network interface, a remote information multiplexer, a remote processor and a remote memory. The remote information interface receives and transmits ultrasonic diagnosis information between the local host and the remote host through the one or more information channels. The remote control interface receives the ultrasonic diagnostic control instructions from the ultrasonic diagnostic expert through the mobile information and control terminal over the one or more control channels. The remote network interface connects the remote host to the communication network. The remote information multiplexer receives, exchanges and transmits the ultrasonic diagnosis information through the one or more information channels in the ultrasonic diagnostic system.

In certain embodiments, the remote memory includes random access memory (RAM) for supporting the operation of the remote processor, and a non-volatile storage device (NVSD). The non-volatile storage device (NVSD) stores an operating system and computer executable instructions. When executed on the remote processor, the computer executable instructions cause the remote processor to perform: establishing network connection to the patient database and the remote host in the second location through the remote network interface over the communication network, and receiving, by the ultrasonic diagnostic technician in the second location, the ultrasonic diagnostic control instructions. The computer executable instructions further cause the remote processor to perform: instructing the ultrasonic diagnostic technician to perform ultrasonic diagnostic examination on the patient interactively according to the ultrasonic diagnostic control instructions, transmitting ultrasonic diagnosis information to the ultrasonic diagnostic expert interactively in real time through the one or more information channels, and receiving, by the ultrasonic diagnostic technician, an ultrasonic diagnosis report of the patient from the ultrasonic diagnostic expert.

These and other aspects of the present disclosure will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the present disclosure, and features and benefits thereof, and together with the written description, serve to explain the principles of the present invention. Wherever possible, the same reference numbers are used throughout the drawings to refer to the same or like elements of an embodiment, and wherein.

DETAILED DESCRIPTION

Figure 1:
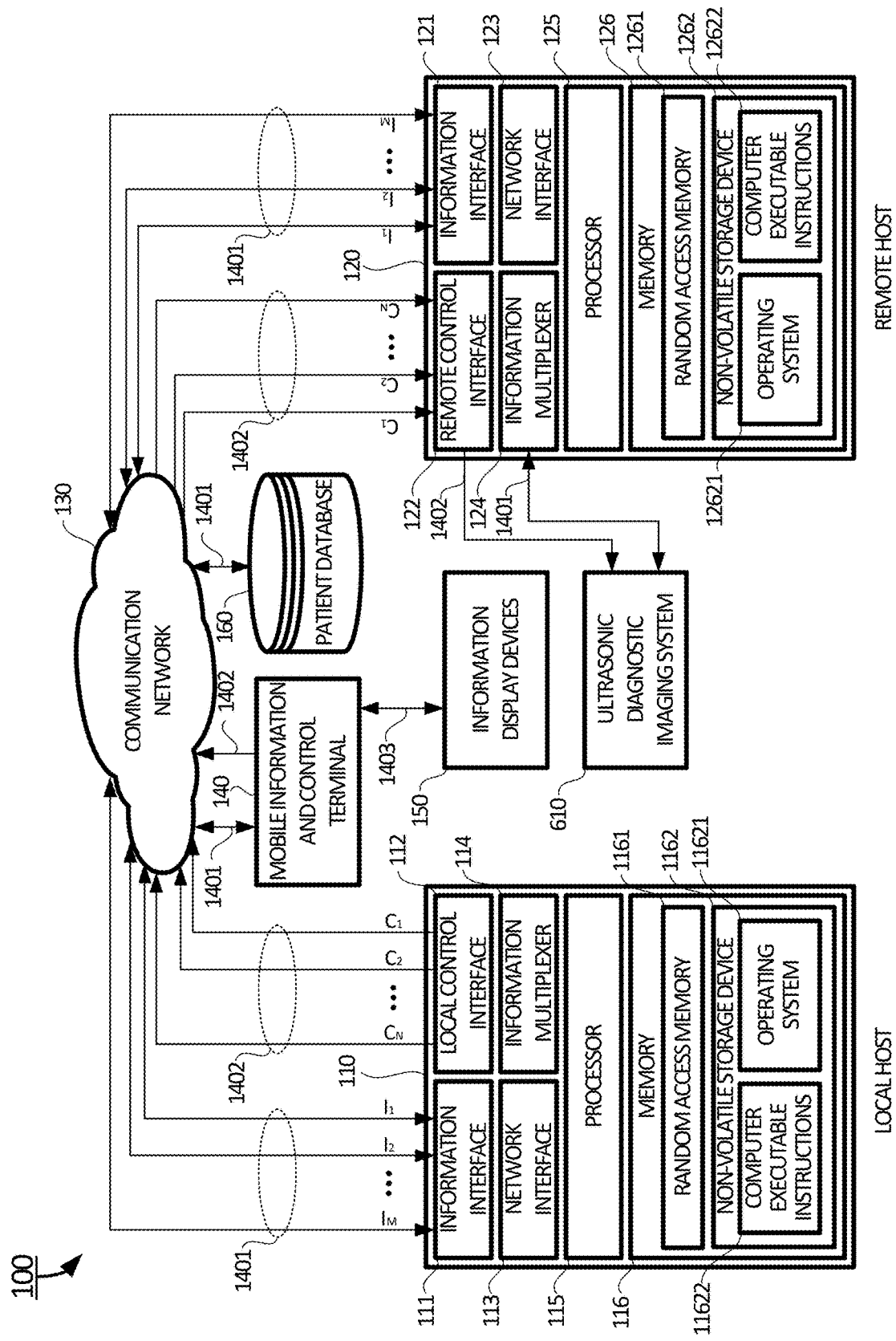
FIG. 1 shows a block diagram of an ultrasonic diagnostic system according to certain embodiments of the present disclosure.

The present disclosure is more particularly described in the following examples that are intended as illustrative only since numerous modifications and variations therein will be apparent to those skilled in the art. Various embodiments of the disclosure are now described in detail. Referring to the drawings, like numbers, if any, indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present disclosure. Additionally, some terms used in this specification are more specifically defined below.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the disclosure or of any exemplified term. Likewise, the disclosure is not limited to various embodiments given in this specification.

Unless otherwise defined, all technical and scientific terms used herein have the same meaning as commonly understood by one of ordinary skill in the art to which this disclosure pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "plurality" means two or more.

As used herein, the terms "comprising," "including," "carrying," "having," "containing," "involving," and the like are to be understood to be open-ended, i.e., to mean including but not limited to.

As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The present disclosure will now be described more fully hereinafter with reference to the accompanying drawings FIGS. 1 through 7, in which embodiments of the disclosure are shown. This disclosure may, however, be embodied in many different forms and should not be construed as limited to the embodiments set forth herein; rather, these embodiments are provided so that this disclosure will be thorough and complete, and will fully convey the scope of the disclosure to those skilled in the art. Like numbers refer to like elements throughout.

Figure 2:
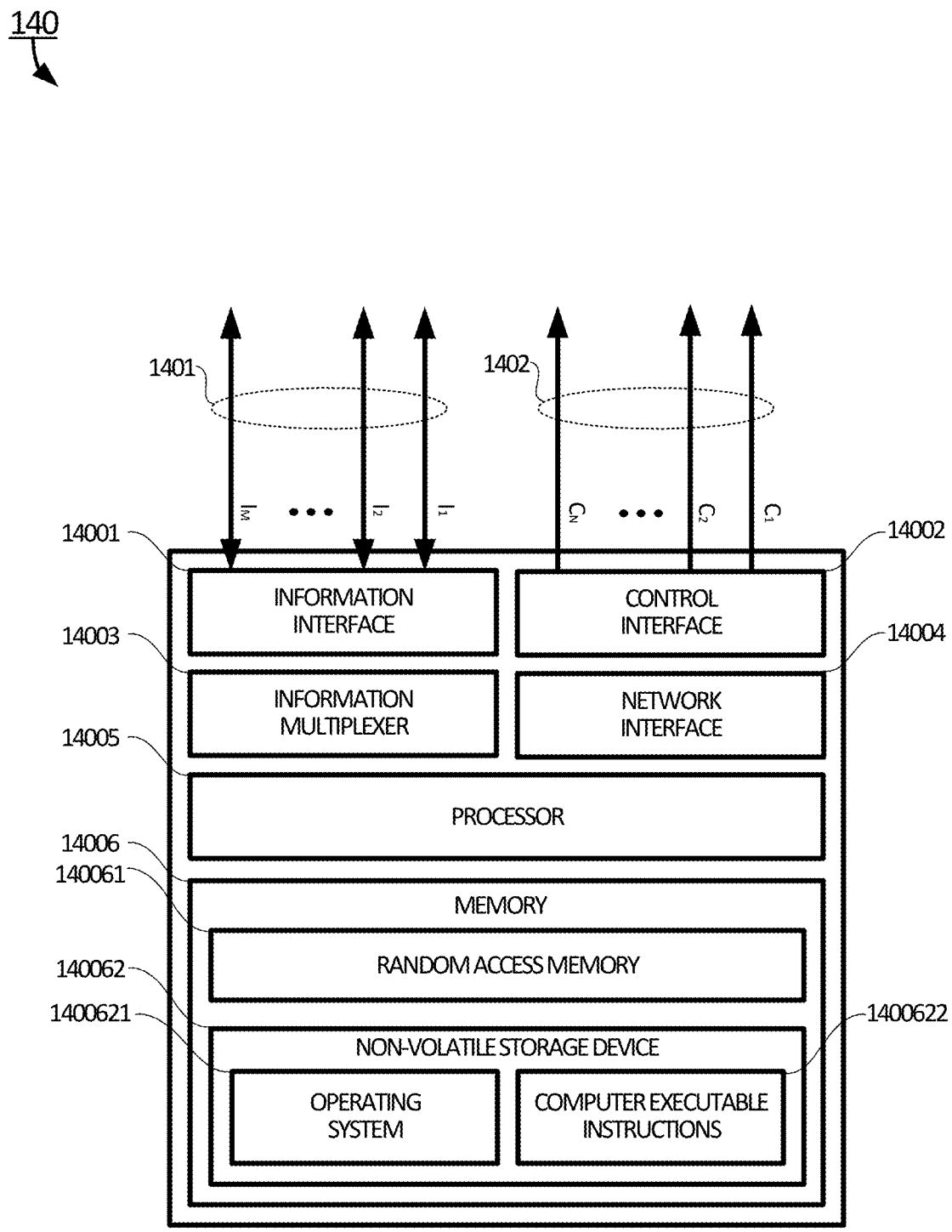
FIG. 2 shows a block diagram of a mobile information and control terminal for the ultrasonic diagnostic system according to certain embodiments of the present disclosure.

In one aspect, the present disclosure relates to a mobile information and control terminal 140 for an ultrasonic diagnostic system 100, as shown in FIG. 2. In certain embodiments, the mobile information and control terminal 140 includes: an information interface 14001, a control interface 14002, an information multiplexer 14003, and a network interface 14004, a processor 14005, and a memory 14006. The information interface 14001 receives and transmits ultrasonic diagnosis information between the mobile information and control terminal 140, a local host 110 in a first location, and a remote host 120 in a second location through one or more information channels 1401. The control interface 14002 receives ultrasonic diagnostic control instructions from an ultrasonic diagnostic expert and transmits the ultrasonic diagnostic control instructions to the local host 110, and the remote host 120 through one or more control channels 1402.

In certain embodiments, the information multiplexer 14003 receives, exchanges and transmits the ultrasonic diagnosis information through the one or more information channels 1401 in the ultrasonic diagnostic system 100. The network interface 14004 connects the mobile information and control terminal 140 to a communication network 130.

In certain embodiments, the processor 14005 includes a shared processor, a dedicated processor, or group of processors and other suitable hardware components, or a combination of some or all of the above, such as in a system-on-chip. The processor 14005 may include single core, dual cores or any other permissible number of cores. In certain embodiments, the memory 14006 includes comprises random access memory (RAM) 140061 for supporting the operation of the processor 14005, and a non-volatile storage device (NVSD) 140062. The NVSD 140062 includes read-only memory, flash memory, ferroelectric RAM, most types of magnetic computer storage devices, for example hard disk drives (HDD), solid state drives (SSD), floppy disks (FD), magnetic tape, and optical discs. The NVSD 140062 stores an operating system 1400621, and computer executable instructions 1400622. The operating system 1400621 includes Microsoft Windows by Microsoft, macOS by Apple Inc, Android by Google, Linux, Unix, and Solaris by Oracle. The processor 14005 executes the computer executable instructions 1400622 for providing the described functionality.

When executed on the processor 14005, the computer executable instructions 1400622 cause the processor 14005 to perform: establishing network connection between the mobile information and control terminal 140, the local host 110 in the first location, a patient database 160 and the remote host 120 in the second location through the network interface 14004 over the communication network 130, and retrieving, by the mobile information and control terminal 140, the patient information of a patient 602 from the patient database 160. The computer executable instructions 1400622 also cause the processor 14005 to perform: instructing, by an ultrasonic diagnostic expert in the first location, an ultrasonic diagnostic technician 601 in the second location using the ultrasonic diagnostic control instructions through the one or more control channels 1402, performing, by the ultrasonic diagnostic technician 601, ultrasonic diagnostic examination on the patient 602 (shown in FIG. 6) interactively according to the ultrasonic diagnostic control instructions, receiving, by the mobile information and control terminal 140, ultrasonic diagnosis information from the ultrasonic diagnostic technician 601 in real time, and generating, via the mobile information and control terminal 140 by the ultrasonic diagnostic expert, an ultrasonic diagnosis report and transmitting the ultrasonic diagnosis report to a doctor of the patient 602 and the patient database 160.

In certain embodiments, the one or more information channels 1401 include: a first information channel $I_1$, a second information channel $I_2$, . . . , and an M-th information channel $I_M$, where M is a positive integer. The one or more information channels 1401 include: one or more patient information channel for transmission of the patient information, one or more information channels from the local host 110 to the remote host 120 for demonstrations by the ultrasonic diagnostic expert, one or more information channels from the remote host 120 to the local host 110 for real time ultrasonic diagnosis by the ultrasonic diagnostic technician 601, and one or more ultrasonic diagnosis report transmission channels.

In certain embodiments, the one or more control channels 1402 include: a first control channel $C_1$, a second control channel $C_2$, . . . , and an N-th control channel $C_N$, wherein N is a positive integer. The one or more control channels 1402 include: one or more audio signal transmission channels, one or more image signal transmission channels, one or more video signal transmission channels, and one or more robotic control signal transmission channels.

In another aspect, the present disclosure relates to an ultrasonic diagnostic system 100, as shown in FIG. 1. In certain embodiments, the ultrasonic diagnostic system 100 includes: a mobile information and control terminal 140, a local host 110 in a first location (local), and a remote host 120 connected to an ultrasonic diagnostic imaging system 170 in a second location (remote). The mobile information and control terminal 140, the local host 110 and remote host 120 are connected through a communication network 130. A patient database 160 is also connected with the communication network 130 allowing the local host 110 and the remote host 120 to access patient information.

In certain embodiments, the mobile information and control terminal 140 is operated by an ultrasonic diagnostic expert in the first location. The mobile information and control terminal 140 retrieves patient information of a patient 602 from the patient database 160, provides ultrasonic diagnostic control instructions from the ultrasonic diagnostic expert in the first location to an ultrasonic diagnostic technician 601 in the second location, receives patient ultrasonic diagnosis information from the remote host 120, and generates and displays ultrasonic diagnosis reports of the patient 602.

In certain embodiments, the local host 110 retrieves the patient information of the patient 602 from the patient database 160 over the communication network 130, provides ultrasonic diagnostic control instructions from the ultrasonic diagnostic expert in the first location to the ultrasonic diagnostic technician 601 in the second location. The ultrasonic diagnostic technician 601 in the second location receives the ultrasonic diagnostic control instructions from the ultrasonic diagnostic expert through the mobile information and control terminal and performs ultrasonic diagnostic examination on the patient 602 according to the ultrasonic diagnostic control instructions received. The ultrasonic diagnostic technician 601 transmits ultrasonic diagnosis information from the remote host 120 to the ultrasonic diagnostic expert in the first location in real time over the communication network 130 interactively. The ultrasonic diagnostic expert then studies the ultrasonic diagnosis information received, generates, transmits and displays ultrasonic diagnosis reports of the patient 602 both at the local host 110 in the first location and at the remote host 120 in the second location, and transmits and stores the ultrasonic diagnosis reports of the patient 602 in the patient database 160.

In certain embodiments, the local host 110 may be connected to an ultrasonic diagnostic imaging system to allow the ultrasonic diagnostic expert to perform certain demonstrations and training operations for the ultrasonic diagnostic technician 601.

In certain embodiments, the communication network 130 includes: a wireless local area network (WLAN), a wireless metropolitan area network (WMAN), a wireless wide area network (WWAN), a cellular network, a mobile communication network, and a wireless personal area network (WPAN), and any combination of these networks. The wireless personal area network includes a Wi-Fi network; a Bluetooth network; an infrared network, and a Zigbee network.

In certain embodiments, the communication network 130 connects the local host 110, the remote host 120, and the patient database 160 through one or more information channels 1401 and one or more control channels 1402.

In certain embodiments, the one or more information channels 1401 includes: a first information channel $I_1$, a second information channel $I_2$, . . . , and an M-th information channel $I_M$, where M is a positive integer. The one or more control channels 1402 includes: a first control channel $C_1$, a second control channel $C_2$, . . . , and an N-th control channel $C_N$, wherein N is a positive integer.

In certain embodiments, the one or more information channels 1401 include: one or more document transmission channels, one or more image transmission channels, and one or more video transmission channels.

In certain embodiments, the one or more information channels 1401 include: one or more patient information channel for transmission of the patient information, one or more information channels from the local host 110 to the remote host 120 for demonstrations by the ultrasonic diagnostic expert, one or more information channels from the remote host 120 to the local host 110 for real time ultrasonic diagnosis by the ultrasonic diagnostic technician 601, and one or more ultrasonic diagnosis report transmission channels.

In certain embodiments, the one or more control channels 1402 include: one or more audio signal transmission channels for transmission of audio commands, one or more image signal transmission channels and one or more video signal transmission channels for live transmission of images or videos showing the maneuvering of the probe 612 or demonstrations. The one or more control channels 1402 may also include one or more robotic control signal transmission channels such that a robot in the second location may perform ultrasonic diagnosis without helps from the ultrasonic diagnostic technician 601.

Figure 3:
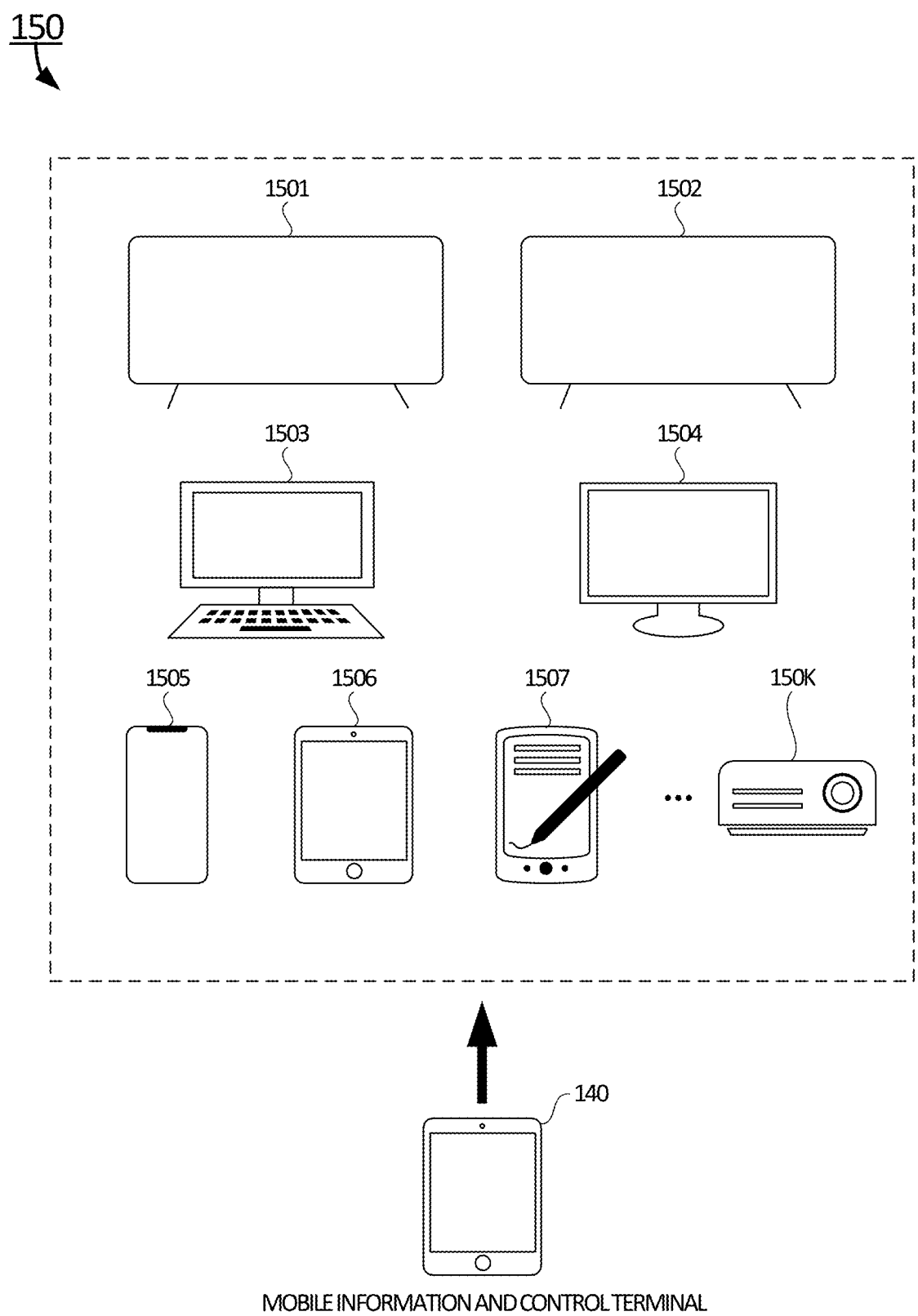
FIG. 3 illustrates various information display devices for the ultrasonic diagnostic system according to certain embodiments of the present disclosure.

In certain embodiments, the mobile information and control terminal 140 further includes one or more information display devices 150. As shown in FIG. 3, the one or more information display devices 150 may include: one or more flat panel televisions (TVs) 1501 and 1502, high definition televisions (HDTVs) 1501 and 1502, and ultra-high-definition televisions (UHDTVs) 1501 and 1502, one or more TVs, HDTVs, and UHDTVs 1501 and 1502 having touch control panels, one or more computer monitors 1503, and one or more computer monitors 1503 having touch control panels. The one or more information display devices 150 may include: one or more smart phones 1505, one or more tablet computers 1506, one or more personal digital assistant (PDA) devices 1507. The one or more information display devices 150 may also include: one or more optical projectors 150K, one or more laser projectors 150K, and any combinations of devices listed above.

Figure 4:
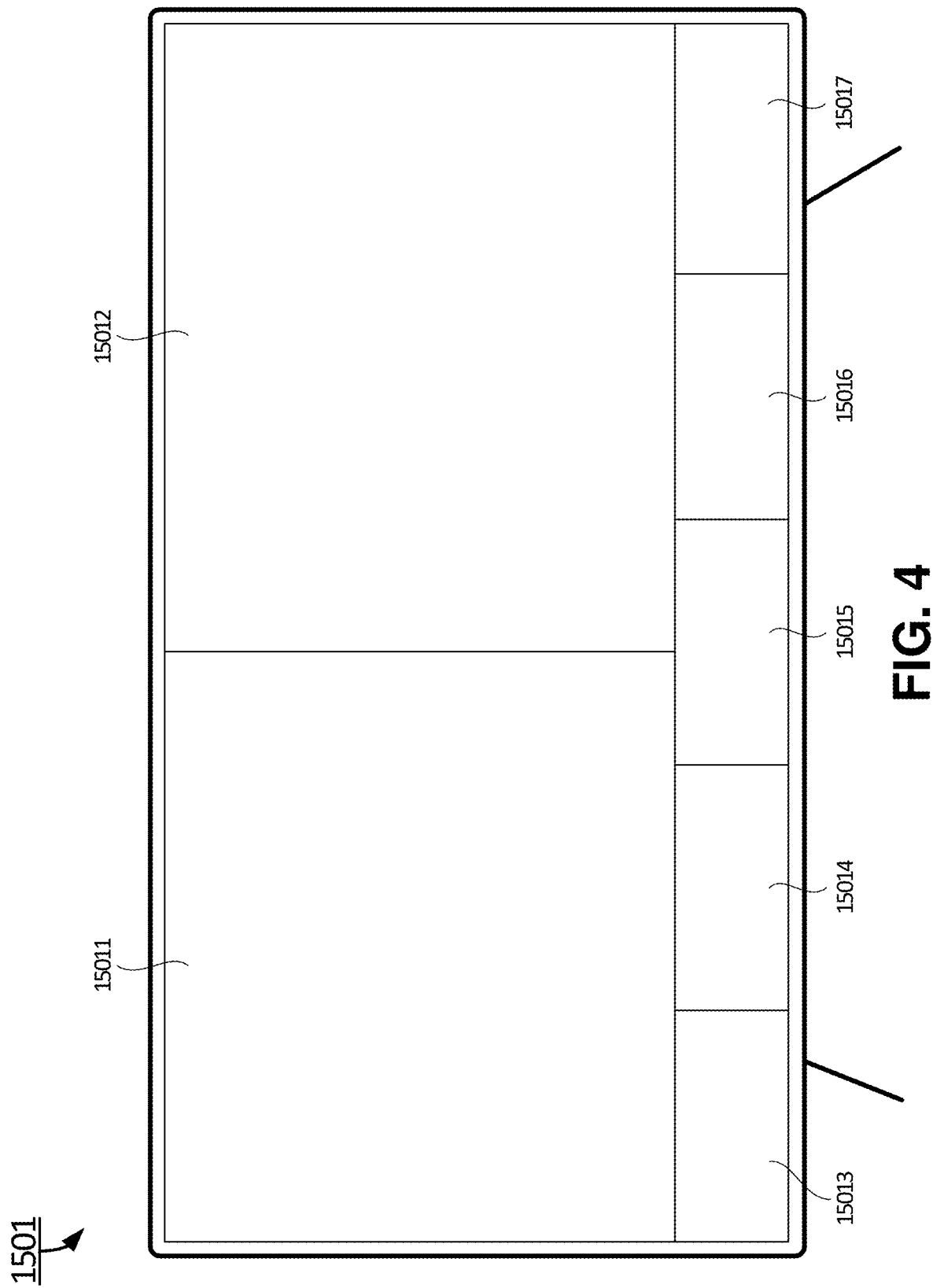
FIG. 4 illustrates each of the information display devices is flexibly partitioned to display information from one or more information channels according to certain embodiments of the present disclosure.

In certain embodiments, as shown in FIG. 4, each of the one or more information display devices 150 is partitioned to display one or more ultrasonic diagnosis information and results from the one or more information channels 1401. For example, the one of the TVs, HDTVs, and UHDTVs 1501 may be partitioned into two large partitions 15011 and 15012, for display two information channels that detailed information needs to be displayed, and five smaller partitions 15013, 15014, 15015, 15016 and 15017, for display five information channels that do not require large screen display.

In certain embodiments, the mobile information and control terminal 140 displays ultrasonic diagnosis information on the one or more information display devices 150 through the one or more information channels 1401. In one embodiment, the mobile information and control terminal 140 displays the ultrasonic diagnosis information on a TV, HDTV, or UHDTV through a cable, or an HDMI cable. In another embodiment, the mobile information and control terminal 140 displays the ultrasonic diagnosis information on a smart TV, a smart HDTV, or a smart UHDTV using Wi-Fi network, Bluetooth network. When the mobile information and control terminal 140 is a smart phone or a tablet, the mobile information and control terminal 140 displays the ultrasonic diagnosis information on a smart TV, a smart HDTV, or a smart UHDTV using screen mirroring, airplay or miracast.

Figure 5:
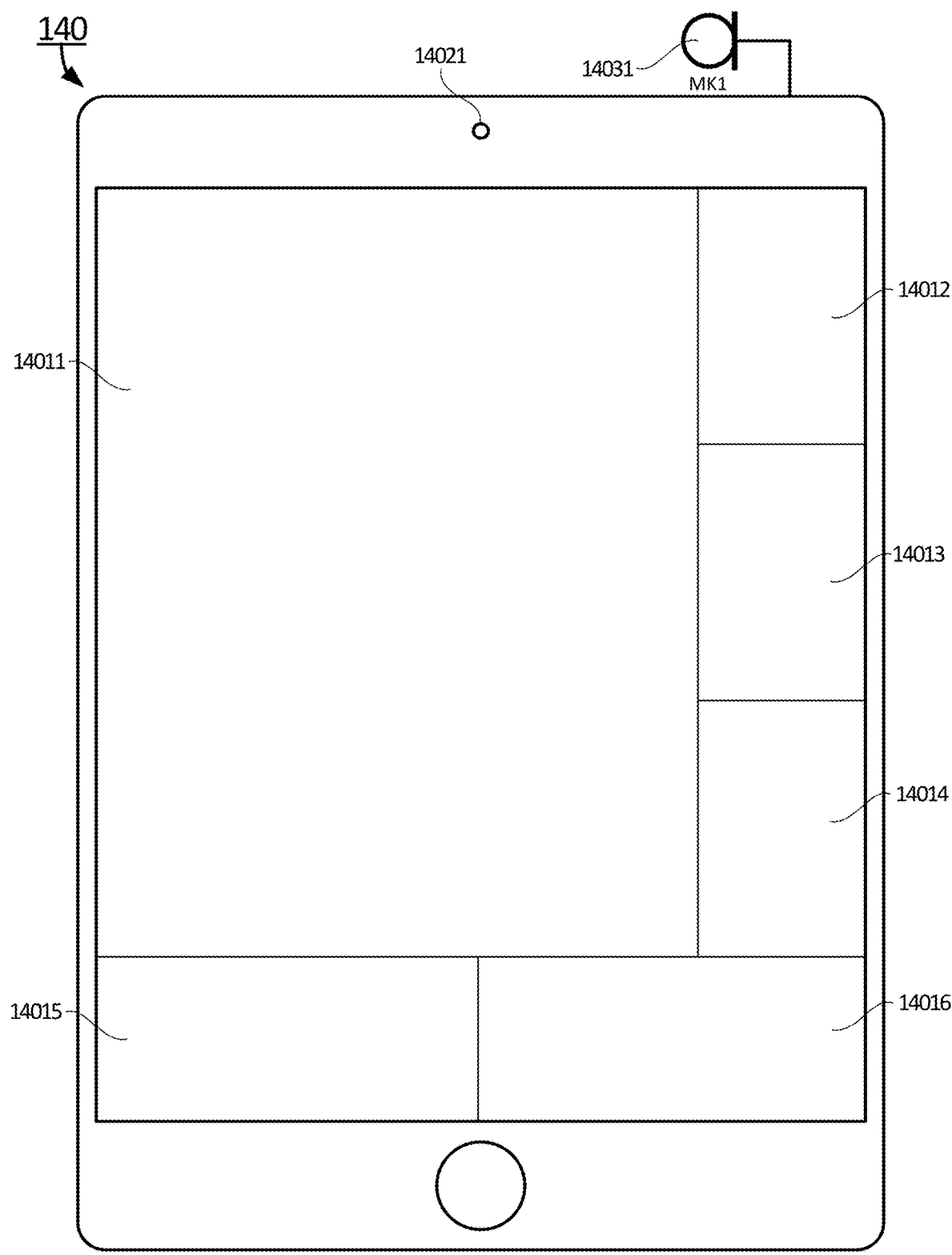
FIG. 5 illustrates the mobile information and control terminal where its display device is flexibly partitioned to display information from one or more information channels according to certain embodiments of the present disclosure.
Figure 6:
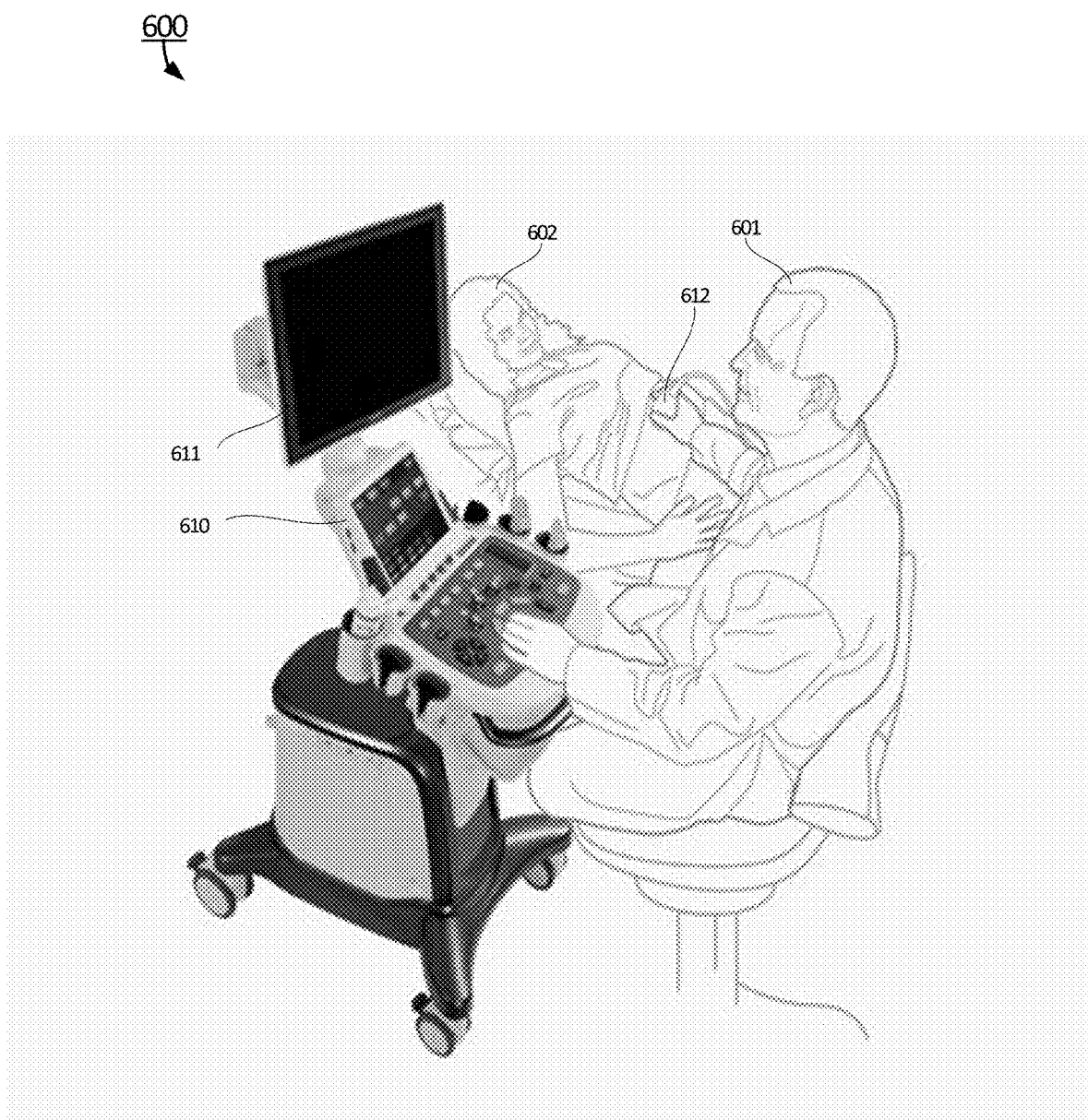
FIG. 6 illustrates an ultrasonic diagnostic technician performing ultrasonic diagnostic procedure on a patient using an ultrasonic diagnostic imaging system in a remote location according to certain embodiments of the present disclosure.

In certain embodiments, as shown in FIG. 5, the mobile information and control terminal 140 has at least one display device 14011. The display device 14011 may be partitioned to display one or more ultrasonic diagnosis information and results from the one or more information channels 1401. For example, the display device 14011 may be partitioned into one large partition 140111 for display one information channel that detailed information needs to be displayed, and four smaller partitions 140112, 140113, 140114, and 140115 for display four information channels that do not require large screen display.

In certain embodiments, the partitions may be flexibly configured such that the size of each partition may be adjusted according to the needs of the ultrasonic diagnostic experts and the ultrasonic diagnostic technicians during the diagnostic procedures in real time.

In certain embodiments, the mobile information and control terminal 140 includes portable laptop computers, tablet computers, and smart phones. These computers and tablets should at least be connected to the internet and/or communication networks 130.

In certain embodiments, the mobile information and control terminal 140 includes one or more camera 14021 for capturing video signals, demonstration video signals, instructional video signals and transmitting these video signals to the remote host 120 and the ultrasonic diagnostic technician 601 for demonstrations and instructions.

In certain embodiments, the mobile information and control terminal 140 includes at least one microphone 14031 for capturing audio signals, demonstration audio signal and instructional audio signals and transmitting these audio signals to the remote host 120 and the ultrasonic diagnostic technician 601 for demonstrations and instructions.

In certain embodiments, the mobile information and control terminal 140 may include a joystick (not shown in FIG. 5) or simulated probe such that the ultrasonic diagnostic expert can use to generate robotic control signal to be transmitted to the remote host 120 and the ultrasonic diagnostic imaging system 610 and to control the robotic arm for performing ultrasonic diagnostic examination on the patient with a robot.

In certain embodiments, the partitions may be flexibly configured such that the size of each partition may be adjusted according to the needs of the ultrasonic diagnostic experts and the ultrasonic diagnostic technicians during the diagnostic procedures in real time.

Referring back to FIG. 1, in certain embodiments, the local host 110 includes: a local information interface 111, a local control interface 112, a local network interface 113, a local information multiplexer 114, a local processor 115 and a local memory 116.

The local information interface 111 receives and transmits ultrasonic diagnosis information between the local host 110 and the remote host 120 through the one or more information channels 1401. The local control interface 112 receives the ultrasonic diagnostic control instructions from the ultrasonic diagnostic expert through the mobile information and control terminal 140 and transmits the ultrasonic diagnostic control instructions to the remote host 120 through the one or more control channels 1402. The local network interface 113 connects the local host 110 to the communication network 130 through the one or more information channels 1401 and the one or more control channels 1402. The local information multiplexer 114 receives, exchanges and transmits the ultrasonic diagnosis information through the one or more information channels 1401 in the ultrasonic diagnostic system 100.

In certain embodiments, the local processor 115 includes a shared processor, a dedicated processor, or group of processors and other suitable hardware components, or a combination of some or all of the above, such as in a system-on-chip. The local processor 115 may include single core, dual cores or any other permissible number of cores. In certain embodiments, the local memory 116 includes comprises random access memory (RAM) 1161 for supporting the operation of the local processor 115, and a non-volatile storage device (NVSD) 1162. The NVSD 1162 includes read-only memory, flash memory, ferroelectric RAM, most types of magnetic computer storage devices, for example hard disk drives (HDD), solid state drives (SSD), floppy disks (FD), magnetic tape, and optical discs. The NVSD 140062 stores an operating system 11621, and computer executable instructions 11622. The operating system 11621 includes Microsoft Windows by Microsoft, macOS by Apple Inc, Android by Google, Linux, Unix, and Solaris by Oracle. The local processor 115 executes the computer executable instructions 11622 for providing the described functionality.

When executed on the local processor 115, the computer executable instructions 11622 cause the local processor 115 to perform: establishing network connection between the mobile information and control terminal 140, the local host 110 in the first location through the local network interface 113, the patient database 160 and the remote host 120 in the second location through a remote network interface 123 over the communication network 130, retrieving, by the local host, the patient information of the patient 602 from the patient database 160. The computer executable instructions 11622 further cause the local processor 115 to perform: instructing, by sending the ultrasonic diagnostic control instructions to the ultrasonic diagnostic technician 601, the ultrasonic diagnostic technician 601 in the second location to perform ultrasonic diagnostic examination on the patient 602 interactively according to the ultrasonic diagnostic control instructions, receiving, from the remote host 120, ultrasonic diagnosis information in real time; generating, by the ultrasonic diagnostic expert, an ultrasonic diagnosis report and transmitting the ultrasonic diagnosis report to a doctor of the patient 602 and the patient database 160.

In certain embodiments, the remote host 120 includes: a remote information interface 121, a remote control interface 122, the remote network interface 123, a remote information multiplexer 124, a remote processor 125 and a remote memory 126.

The remote information interface 121 receives and transmits ultrasonic diagnosis information between the local host 110 and the remote host 120 through the one or more information channels 1401. The remote control interface 122 receives the ultrasonic diagnostic control instructions from the ultrasonic diagnostic expert through the mobile information and control terminal 140 over the one or more control channels 1402. The network interface 123 connects the remote host 120 to the communication network 130 through the one or more information channels 1401 and the one or more control channels 1402. The information multiplexer 124 receives, exchanges and transmits the ultrasonic diagnosis information through the one or more information channels 1401 in the ultrasonic diagnostic system 100.

In certain embodiments, the remote processor 125 includes a shared processor, a dedicated processor, or group of processors and other suitable hardware components, or a combination of some or all of the above, such as in a system-on-chip. The remote processor 125 may include single core, dual cores or any other permissible number of cores. In certain embodiments, the remote memory 126 includes comprises random access memory (RAM) 1261 for supporting the operation of the remote processor 125, and a non-volatile storage device (NVSD) 1262. The NVSD 1262 includes read-only memory, flash memory, ferroelectric RAM, most types of magnetic computer storage devices, for example hard disk drives (HDD), solid state drives (SSD), floppy disks (FD), magnetic tape, and optical discs. The NVSD 1262 stores an operating system 12621, and computer executable instructions 12622. The operating system 12621 includes Microsoft Windows by Microsoft, macOS by Apple Inc, Android by Google, Linux, Unix, and Solaris by Oracle. The remote processor 125 executes the computer executable instructions 11622 for providing the described functionality.

When executed on the remote processor 125, the computer executable instructions 12622 cause the remote processor 125 to perform: establishing network connection between the mobile information and control terminal 140, the local host 110 in the first location through the local network interface 113, the patient database 160 and the remote host 120 in the second location through the remote network interface 123 over the communication network 130, receiving, by the ultrasonic diagnostic technician 601 in the second location, the ultrasonic diagnostic control instructions, performing, by the ultrasonic diagnostic technician 601, ultrasonic diagnostic examination on the patient 602 interactively according to the ultrasonic diagnostic control instructions; transmitting, by the ultrasonic diagnostic technician 601, ultrasonic diagnosis information in real time to the ultrasonic diagnostic expert through the one or more information channels 1401, and receiving, by the ultrasonic diagnostic technician 601, ultrasonic diagnosis report from the ultrasonic diagnostic expert.

In yet another aspect, the present disclosure relates to a method of using an ultrasonic diagnostic system 100. In certain embodiments, the method includes: installing a local host 110 in a first location where an ultrasonic diagnostic expert is performing ultrasonic diagnosis using ultrasonic diagnostic control instructions via a mobile information and control terminal 140, installing a remote host 120 in a second location where an ultrasonic diagnostic technician 601 is performing ultrasonic diagnosis on a patient 602 using an ultrasonic diagnostic imaging system 170 according to the ultrasonic diagnostic control instructions, connecting the local host 110, the remote host 120, a patient database 160 to a communication network 130 through one or more information channels 1401 and one or more control channels 1402, and retrieving, by the local host 110, patient information of the patient 602 from the patient database 160 and displaying the retrieved patient information to the ultrasonic diagnostic expert.

In certain embodiments, the method also includes: providing, by the ultrasonic diagnostic expert in the first location, the ultrasonic diagnostic control instructions to the ultrasonic diagnostic technician 601 through the one or more control channels 1402, receiving, by the ultrasonic diagnostic technician 601 in the second location, the ultrasonic diagnostic control instructions and performing ultrasonic diagnostic examination on the patient 602 interactively according to the ultrasonic diagnostic control instructions received, transmitting, by the ultrasonic diagnostic technician 601, ultrasonic diagnosis information to the ultrasonic diagnostic expert in real time through the one or more information channels 1401, and generating, by the ultrasonic diagnostic expert, an ultrasonic diagnosis report, and transmitting the ultrasonic diagnosis report to a doctor of the patient 602 and the patient database 160.

Figure 7:
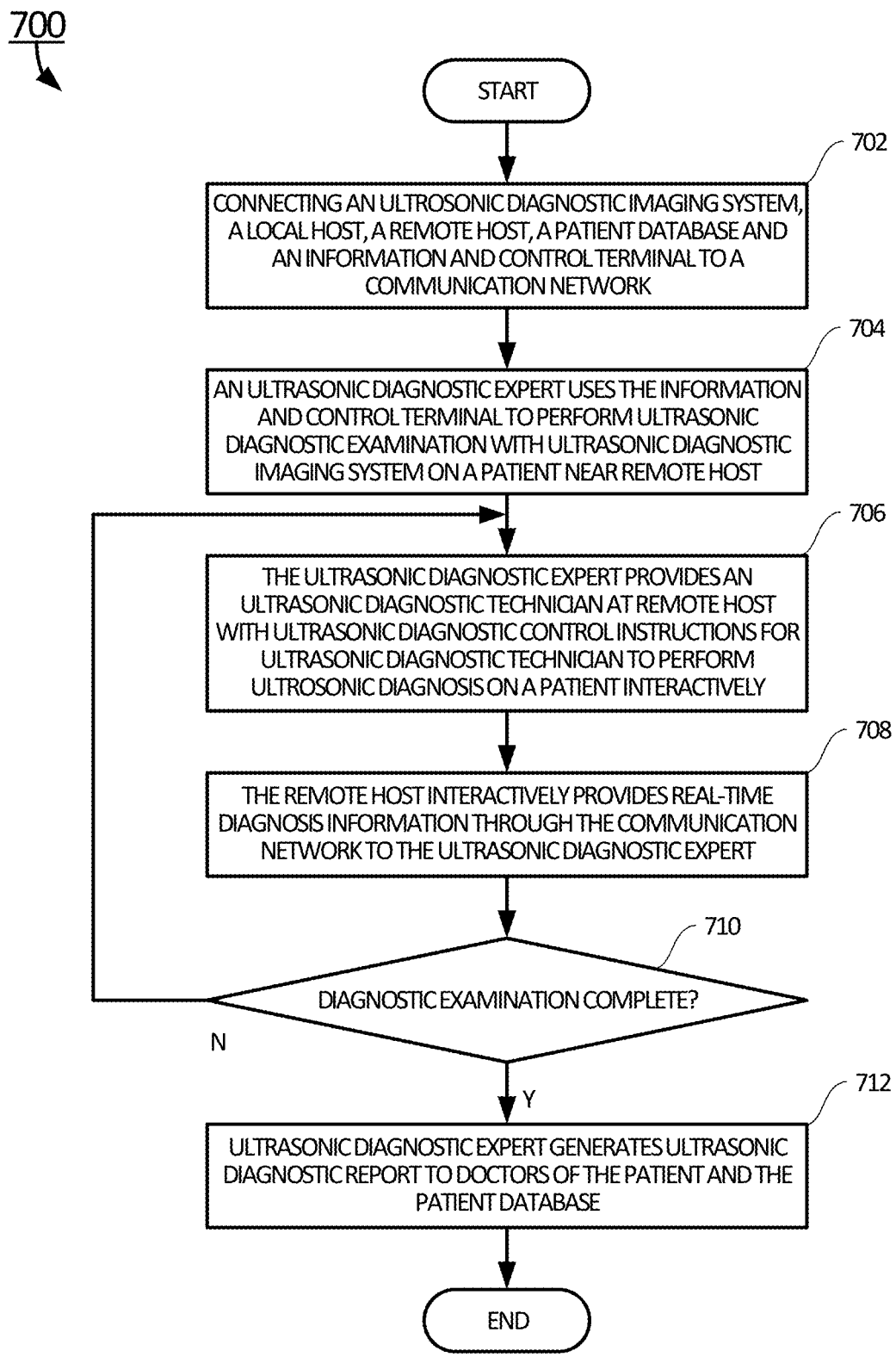
FIG. 7 shows a flow chart of a method of using the ultrasonic diagnostic system according to certain embodiments of the present disclosure.

Referring now to FIG. 7, a flow chart 700 of a method of using the ultrasonic diagnostic system is shown according to certain embodiments of the present disclosure.

At block 702, after the local host 110 is installed in the first location and connected to the mobile information and control terminal 140 through the communication network 130, the remote host 120 is installed in the second location and connected to the ultrasonic diagnostic imaging system 610, and the patient database 160 is installed, the communication network 130 is used to connect the local host 110, the remote host 120, and the patient database 160 through one or more information channels 1401 and one or more control channels 1402.

In certain embodiments, the local host 110 includes: a local information interface 111, a local control interface 112, a local network interface 113, a local information multiplexer 114, a local processor 115 and a local memory 116.

In certain embodiments, the remote host 120 includes: a remote information interface 121, a remote control interface 122, a remote network interface 123, a remote information multiplexer 124, a remote processor 125 and a remote memory 126.

In certain embodiments, the mobile information and control terminal 140 further includes one or more information display devices 150. Each of the one or more information display devices 150 is partitioned to display one or more ultrasonic diagnosis information and results from the one or more information channels 1401.

At block 704, an ultrasonic diagnostic expert uses the mobile information and control terminal 140 to perform ultrasonic diagnostic examination with the ultrasonic diagnostic imaging system on a patient 602 at the remote host 120 in the second location.

At block 706, the ultrasonic diagnostic expert provides ultrasonic diagnostic control instructions to an ultrasonic diagnostic technician 601 over the communication network 130 through the one or more control channels 1402. The ultrasonic diagnostic control instructions provided allow the ultrasonic diagnostic technician 601 to perform ultrasonic diagnostic examination on the patient at the remote host 120 in the second location.

At block 708, the remote host 120 interactively provides real time ultrasonic diagnosis information back to the ultrasonic diagnostic expert over the communication network 130 through the one or more information channels 1401.

The block 706 and block 708 form a loop that can be repeated many time until the ultrasonic diagnostic expert obtains satisfactory results of the ultrasonic diagnostic examination.

At query block 710, the ultrasonic diagnostic expert is asked whether the ultrasonic diagnostic examination is competed. When the ultrasonic diagnostic examination is completed, the method proceeds to block 712. When more ultrasonic diagnostic examination is desired, the method proceeds to block 706 and continues to perform the ultrasonic diagnostic examination.

At block 712, once the ultrasonic diagnostic examination is completed, the ultrasonic diagnostic expert prepares ultrasonic diagnostic report, and sends the ultrasonic diagnostic report to doctors of the patient 602 and the patient database 160.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. A method of using an ultrasonic diagnostic system, comprising:
   installing a local host in a first location where an ultrasonic diagnostic expert is performing ultrasonic diagnosis using ultrasonic diagnostic control instructions via a mobile information and control terminal;
   installing a remote host in a second location where an ultrasonic diagnostic technician is performing ultrasonic diagnostic examination on a patient using an ultrasonic diagnostic imaging system according to the ultrasonic diagnostic control instructions from the ultrasonic diagnostic expert;
   connecting the mobile information and control terminal, the local host, the remote host, a patient database to a communication network through a plurality of information channels and a plurality of control channels;
   retrieving, by the mobile information and control terminal, patient information of the patient from the patient database and displaying the retrieved patient information to the ultrasonic diagnostic expert;
   providing, by the ultrasonic diagnostic expert in the first location, ultrasonic diagnostic control instructions to the ultrasonic diagnostic technician through the plurality of control channels;
   receiving, by the ultrasonic diagnostic technician in the second location, the ultrasonic diagnostic control instructions and performing ultrasonic diagnostic examination on the patient interactively according to the ultrasonic diagnostic control instructions;
   transmitting, by the ultrasonic diagnostic technician, ultrasonic diagnosis information to the ultrasonic diagnostic expert interactively in real time through the plurality of information channels; and
   generating, by the ultrasonic diagnostic expert, an ultrasonic diagnosis report, and transmitting the ultrasonic diagnosis report to a doctor of the patient and the patient database.

2. The method according to claim 1, wherein the communication network comprises:
   a wireless personal area network (WPAN) having a Wi-Fi network; a Bluetooth network; an infrared network, and a Zigbee network,
   a wireless local area network (WLAN);
   a wireless metropolitan area network (WMAN);
   a wireless wide area network (WWAN);
   a cellular network;
   a mobile communication network; and
   any combinations thereof.

3. The method according to claim 1, wherein the plurality of information channels comprises a first information channel I1, a second information channel I2, . . . , and an M-th information channel IM, where M is a positive integer, wherein the plurality of information channels comprises:
   one or more patient information channel for transmission of the patient information;
   one or more information channels from the local host to the remote host for demonstrations by the ultrasonic diagnostic expert;
   one or more information channels from the remote host to the local host for real time ultrasonic diagnosis by the ultrasonic diagnostic technician; and
   one or more ultrasonic diagnosis report transmission channels.

4. The method according to claim 1, wherein the plurality of control channels comprises a first control channel $C_1$, a second control channel $C_2$, . . . , and an N-th control channel $C_N$, where N is a positive integer, wherein the plurality of control channels comprises:
   one or more audio signal transmission channels;
   one or more image signal transmission channels;
   one or more video signal transmission channels; and
   one or more robotic control signal transmission channels.

5. The method according to claim 1, wherein the mobile information and control terminal further comprises one or more information display devices, wherein each of the one or more information display devices is partitioned to display one or more ultrasonic diagnosis information and results from the plurality of information channels.

6. The method according to claim 5, wherein the one or more information display devices comprise at least one of:
   a flat panel televisions (TV), high definition televisions (HDTV), and ultra-high-definition televisions (UHDTV);
   a TV, HDTV, and UHDTV having touch control panel;
   a computer monitor;
   a computer monitor having touch control panel;
   a smart phone;
   a tablet computer;
   a personal digital assistant (PDA) device;
   an optical projector;
   a laser projector.

7. The method according to claim 6, wherein the local host comprises:
- a local information interface for receiving and transmitting ultrasonic diagnosis information between the local host and the remote host through the plurality of information channels;
- a local control interface for receiving the ultrasonic diagnostic control instructions from the mobile information and control terminal and transmitting the ultrasonic diagnostic control instructions to the remote host through the plurality of control channels;
- a local network interface for connecting the local host to the communication network;
- a local information multiplexer for receiving, exchanging and transmitting the ultrasonic diagnosis information through the plurality of information channels in the ultrasonic diagnostic system;
- a local processor and a local memory, wherein the local memory comprises double data rate (DDR) random access memory (RAM) for supporting the operation of the local processor, a non-volatile storage device (NVSD) storing an operating system, and computer executable instructions, when executed on the local processor, the computer executable instructions cause the local processor to perform:
- establishing network connection between the mobile information and control terminal, the local host in the first location through the local network interface, the patient database and the remote host in the second location through a remote network interface over the communication network;
- retrieving, by the local host, the patient information of the patient from the patient database;
- instructing, by sending the ultrasonic diagnostic control instructions to an ultrasonic diagnostic technician, the ultrasonic diagnostic technician in the second location to perform ultrasonic diagnostic examination on the patient interactively according to the ultrasonic diagnostic control instructions;
- receiving, from the remote host, ultrasonic diagnosis information interactively in real time; and
- generating, by the ultrasonic diagnostic expert, an ultrasonic diagnosis report and transmitting the ultrasonic diagnosis report to the doctor of the patient and the patient database.

8. The method according to claim 7, wherein the remote host comprises:
- a remote information interface for receiving and transmitting ultrasonic diagnosis information between the local host and the remote host through the plurality of information channels;
- a remote control interface for receiving the ultrasonic diagnostic control instructions from the mobile information and control terminal through the plurality of control channels;
- the remote network interface for connecting the remote host to the communication network;
- a remote information multiplexer for receiving, exchanging and transmitting the ultrasonic diagnosis information through the plurality of information channels;
- a remote processor and a remote memory, wherein the remote memory comprises double data rate (DDR) random access memory (RAM) for supporting the operation of the remote processor, a non-volatile storage device (NVSD) storing an operating system, and computer executable instructions, when executed on the remote processor, the computer executable instructions cause the remote processor to perform:
- establishing network connection to the patient database and the remote host in the second location through the remote network interface over the communication network;
- receiving, by the ultrasonic diagnostic technician in the second location, the ultrasonic diagnostic control instructions;
- performing, by the ultrasonic diagnostic technician, ultrasonic diagnostic examination on the patient interactively according to the ultrasonic diagnostic control instructions;
- transmitting, by the ultrasonic diagnostic technician, ultrasonic diagnosis information to the ultrasonic diagnostic expert interactively in real time through the plurality of information channels; and
- receiving, by the ultrasonic diagnostic technician, an ultrasonic diagnosis report of the patient from the ultrasonic diagnostic expert.

* * * * *